US005549110A

United States Patent [19]

Krauss et al.

[11] Patent Number: 5,549,110

[45] Date of Patent: Aug. 27, 1996

[54] DEVICE FOR GENERATING SOUND IMPULSES FOR MEDICAL APPLICATIONS

[75] Inventors: Werner Krauss, Knittlingen; Jan Zwingenberger, Mainz; Peter Jaggy, Ötisheim, all of Germany

[73] Assignee: Richard Wolf GmbH, Knittlingen, Germany

[21] Appl. No.: 206,073

[22] Filed: Mar. 4, 1994

[30] Foreign Application Priority Data

Mar. 11, 1993 [DE] Germany .......................... 43 07 669.6

[51] Int. Cl.$^6$ .......................... A61B 8/00

[52] U.S. Cl. .......................... 128/661.01

[58] Field of Search .......................... 128/660.08, 661.01; 601/2, 3; 310/327, 328, 331, 332, 334; 73/620, 625, 626

[56] References Cited

U.S. PATENT DOCUMENTS

| | | | |
|---|---|---|---|
| 5,101,133 | 3/1992 | Schäfer | 310/355 |
| 5,111,805 | 5/1992 | Jaggy et al. | 128/24 |
| 5,410,205 | 4/1995 | Gururaja | 310/328 |

FOREIGN PATENT DOCUMENTS 0372198 6/1990 European Pat. Off. .

*Primary Examiner*—George Manuel
*Attorney, Agent, or Firm*—Panitch Schwarze Jacobs & Nadel, P.C.

[57] ABSTRACT

A device, which is especially made for the generation of shockwaves to detect inner-body objects, is equipped with piezo-ceramic transducer elements which act as an electro-acoustical transducer which can be driven by a high-voltage source with high-voltage impulses to generate shock waves or sound impulses through directed deformations and length changes of the transducer elements is dependent on the given polarization of the transducer elements and the polarity of the high-voltage impulses. The sound energy emitted by the device may then be especially high if the transducer elements are excited and biased with a bias potential before the appearance of a high-voltage impulse and the polarity of the bias potential is opposite to that of the high-voltage impulse.

7 Claims, 7 Drawing Sheets

U
-U
t
19
19

U
-U
t
15
15

U
-U
t
16
16
Δt

U
-U
t
20
Δt

DEVICE FOR GENERATING SOUND IMPULSES FOR MEDICAL APPLICATIONS

FIELD OF THE INVENTION

The invention relates to the use of piezo-ceramic transducer elements as electro-acoustic transducers for generating sound impulses for medical applications, specifically shock waves for the detection of inner-body objects. These transducers are driven by a high-voltage source with high-voltage impulses to generate sound impulses through directed changes in length of the transducer elements, dependent on the given polarization of the transducer elements and the polarity of the high-voltage impulse.

BACKGROUND OF THE INVENTION

Known devices of this kind (see, for example, DE-C 39 32 959, DE-A 40 00 362, and EP-A 0 372 198) have proved successful, especially in extracorporeal lithotripsy, because they offer a tissue-friendly and pain-free form of therapy and guarantee, as well, a specific and effective detection of such objects as ureter and kidney stones.

However, the desire to be able to work even more effectively in specific application areas (e.g., the destruction of deep-lying ureter stones) prompts a need for additional power reserves (RC) regarding sound energy. In principle, other therapy forms (e.g., the stimulation of bone tissues and the treatment of pseudoarthritis) will also require higher powers than were possible up to now.

Increases in power are attained by applying new and improved piezo-ceramics or also by optimal acoustic adaptations, but these are, in general, relatively expensive. Further, the power of devices can also be increased by increasing the high-voltage impulses that drive the transducer elements. Increasing the high-voltage impulses is achieved only at the expense of the lifespan of the transducer elements. It also places maximum demands on the isolation efficacy because the contacts and electrodes of the transducer elements can no longer be reliably isolated electrically with respect to each other. In addition, when high-voltage impulses are increased, the power of the device can only be increased to a limited degree, because otherwise the intensity of the electrical field between the contacts of the transducer elements would become too high. Furthermore, the regulation and changes in length of the transducer elements would no longer be proportional to the applied voltage, and finally, the ceramic could be destroyed.

SUMMARY OF THE INVENTION

It is an object of the invention to simply and inexpensively realize the possibility of increasing the acoustic power of the above-mentioned devices. This object is achieved according to the invention for devices of this kind in such a way that before the arrival of each high-voltage impulse the transducer elements are excitable with a bias voltage (pre-voltage) whose polarity is opposite to the polarity of the high-voltage impulse.

If, for example, transducer elements are to generate positive pressure impulses as acoustically applied impulses for detection of objects, the transducer elements are first biased negatively with a bias voltage so that a negatively directed electrical field is built up within the elements, and the length of the transducer element is reduced from a neutral starting configuration. Also associated with such a bias potential: 1) the reciprocal piezo-electric effect is used in such a way that the transducer elements are negatively biased, not only via the correspondingly directed electrical field but also in a quasi-mechanical fashion, and 2) the position of the emission surface is altered through a negative offset. This requires that the polarity of the bias voltage and intensity of the field, as well as the polarization of the ceramic material, are correspondingly matched with one another. This is essentially a question of the polarization of the ceramic material, from which the determination of the polarity of the bias potential as well as that of the high-voltage impulse proceeds.

After negative biasing of the transducer elements the elements are driven by the short, transient, and positive high-voltage impulse, and upon release of a positive pressure impulse they become deformed from the arbitrarily produced deformation in the emission direction. A reverse process is followed when negative pressure impulses or tension impulses are to be generated. In this case, the transducer elements are biased positively in such a way that their length is first enlarged by a positive offset in comparison to the neutral starting configuration, while after that the transducer elements are excited by negative high-voltage impulses, and their length is suddenly reduced. This causes a negative acoustic impulse.

Assuming that the transducer elements are only to be excited with, for example, a high voltage as large as the voltage of the high-voltage impulse of conventional devices with smaller acoustical capacity, the present invention allows for the reduction of the maximum voltage applied to the transducer elements by the amount of the voltage of the bias, and can thereby also reduce the risk of voltage-overload among the electrodes of the transducer elements.

It is also possible to displace the region of required deformations and adjustments of the transducer elements to another region in which the adjustments are proportional to the high voltage applied.

Finally, the power of the device can also be increased, because due to the biasing of the transducer elements a short rising time is achieved for their deformation and adjustments, as soon as the respective high-voltage impulse arrives. This is possible because of the tendency of the ceramic material to return from the biased condition to the neutral condition, whereby the acceleration of the deformation is higher than when the transducer elements are driven, as before, from a neutrally-charged condition.

The bias potential can be a permanent direct-current voltage, superimposed by the high-voltage impulses, which are greater in their absolute voltage value. On the other hand, the bias potential can also have an impulse form, and in this case can essentially be turned off at the time of the beginning or arrival of a high-voltage impulse. Because the transducer elements react like RC-modules with a time constant $\tau \approx R \times C$, the use of bias-potential impulses with their time length $\Delta t$ and the time constant $\tau$ should fulfill the relationship $\Delta t \geqq 5\tau$, so that the transducer elements can be biased to the required value in good time before the occurrence of high-voltage impulses.

In addition to the aforementioned first high-voltage source for driving the device, a second high-voltage source is provided for generating the bias for the transducer elements. The first high-voltage source is connectable to the transducer elements via a triggerable switch.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE PREFERRED EMBODIMENTS

Figure 7:
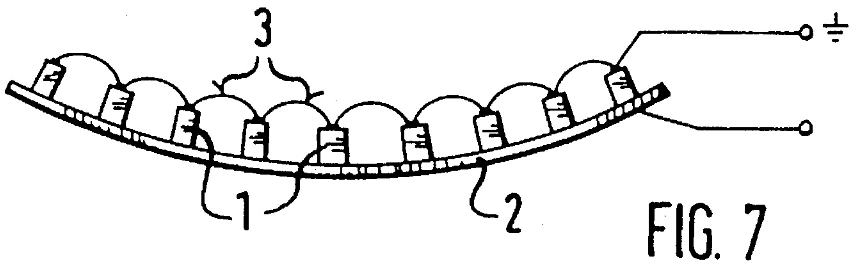
FIGS. 7 through 10 show schematically diverse embodiments of electro-acoustical transducers.

According to FIG. 7, the transducer elements 1 can be so arranged standing in a mosaic arrangement on a carrier 2 such that, due to the spherical cap form of the carrier, the axes of the transducer elements meet each other at a point, namely the focus of the transducer. In this case, the transducer has a self-focusing design.

The transducer elements have contacts on top on the emission side, by means of which they are connected to each other through grounded wires 3. The opposite ends of the transducer elements are connected to the carrier 2, which consists of electrical-conducting material. The carrier is also connected to the high-voltage source (to be described later) that generates the high-voltage impulses and the bias potential.

Figure 8:
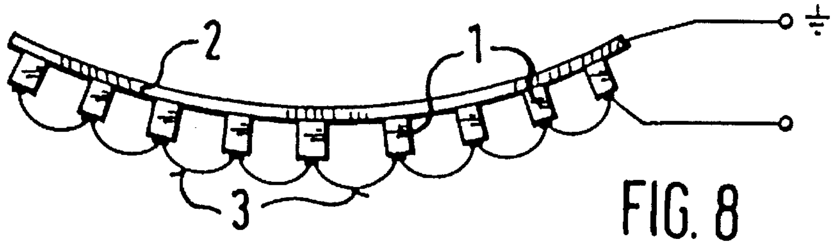

In the likewise self-focusing transducers according to FIG. 8, the transducer elements 1 are situated on the underside of the grounded carrier 2 so that in this case, the opposite side of the carrier forms the emission surface. The electrical contacts and connections of the transducer elements with the wires 3 are designed as in the transducer shown in FIG. 7 and connected to the outputs of the high-voltage sources.

Figure 9:
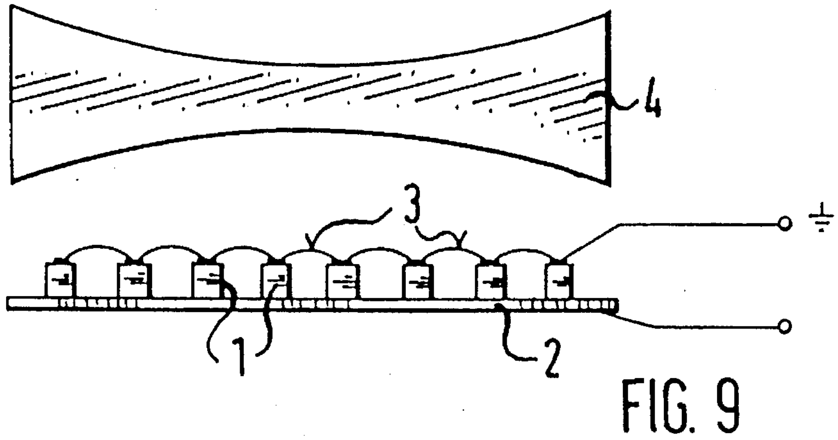
Figure 10:
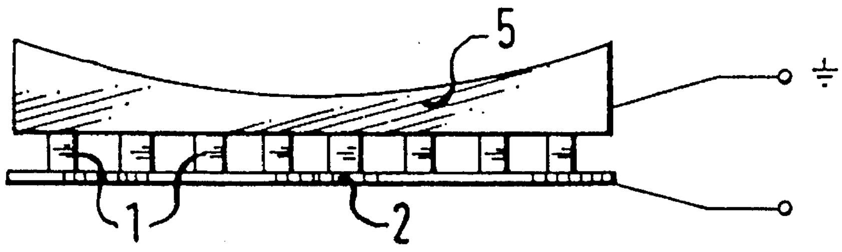

In the planar transducer according to FIG. 9, the transducer elements 1 are fastened to a flat carrier 2 in such a way that the sound impulses are given off along parallel axes of the transducer elements and must be focused with an acoustic lens 4, in cases where focusing of the transducer is required. If a metallic focus lens 5 is used corresponding to FIG. 10, separate connection wires can be omitted, because the lens which electrically connects the upper ends of the transducer elements can assume their functions. The other ends of the transducer elements are connected via the metallic carrier 2 in such a way that all transducer elements are in effect wired in an electrically parallel fashion, as was the case with the three previously described types of transducers.

In all cases, the polarizing of the voltages by which the transducer elements are driven, and the polarizing of the connections of the transducer elements, act in accordance with how they are polarized and whether positive pressure impulses or negative tension impulses are to be generated. This is known and therefore need not be explained further.

Figure 1:
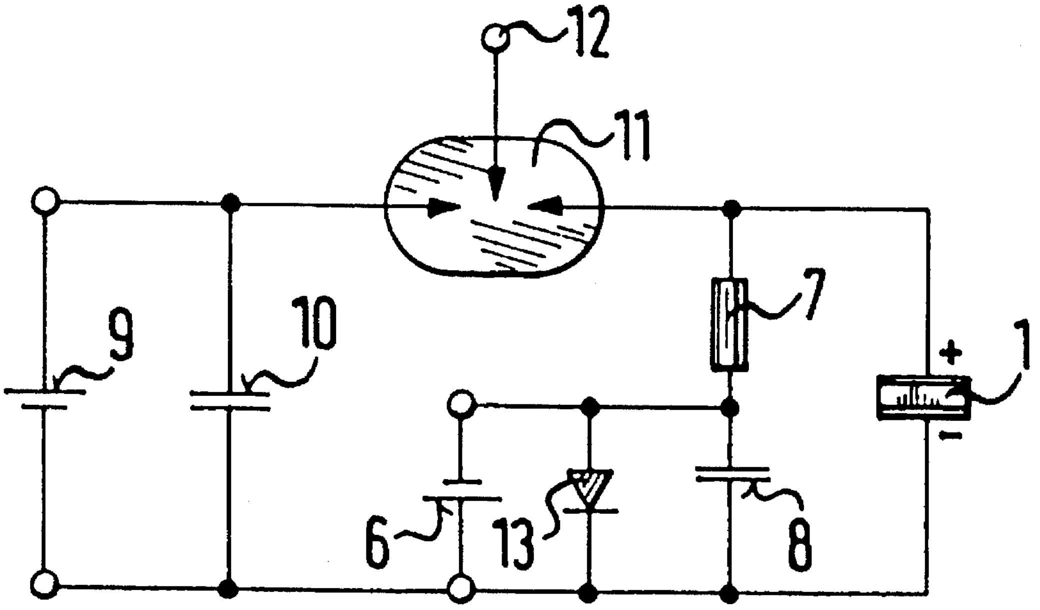
FIG. 1 illustrates a circuit with high-voltage sources for generating high-voltage impulses and the bias potential.
Figures 2A, 2B, 2C, 2D:
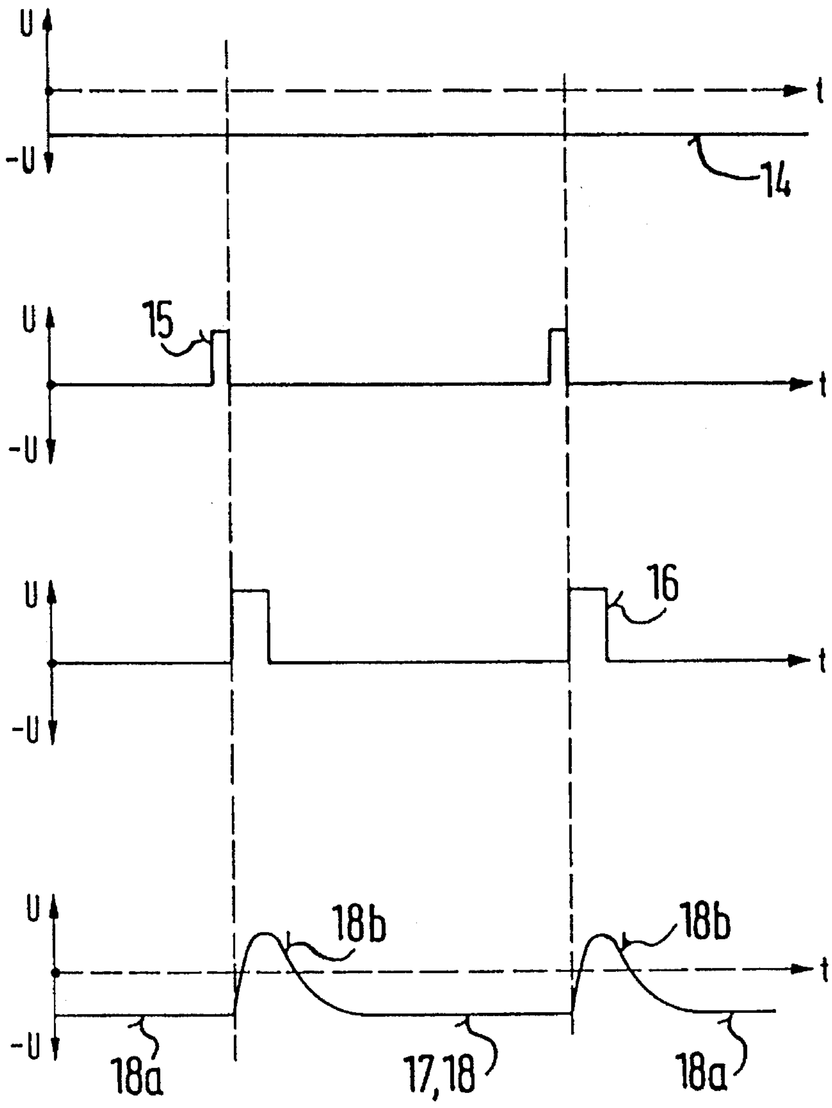
FIGS. 2A–D, 3A–D, 4A–D and 5A–D show time traces of voltages in the circuit of the device and at the transducer elements.
Figures 3A, 3B, 3C, 3D:
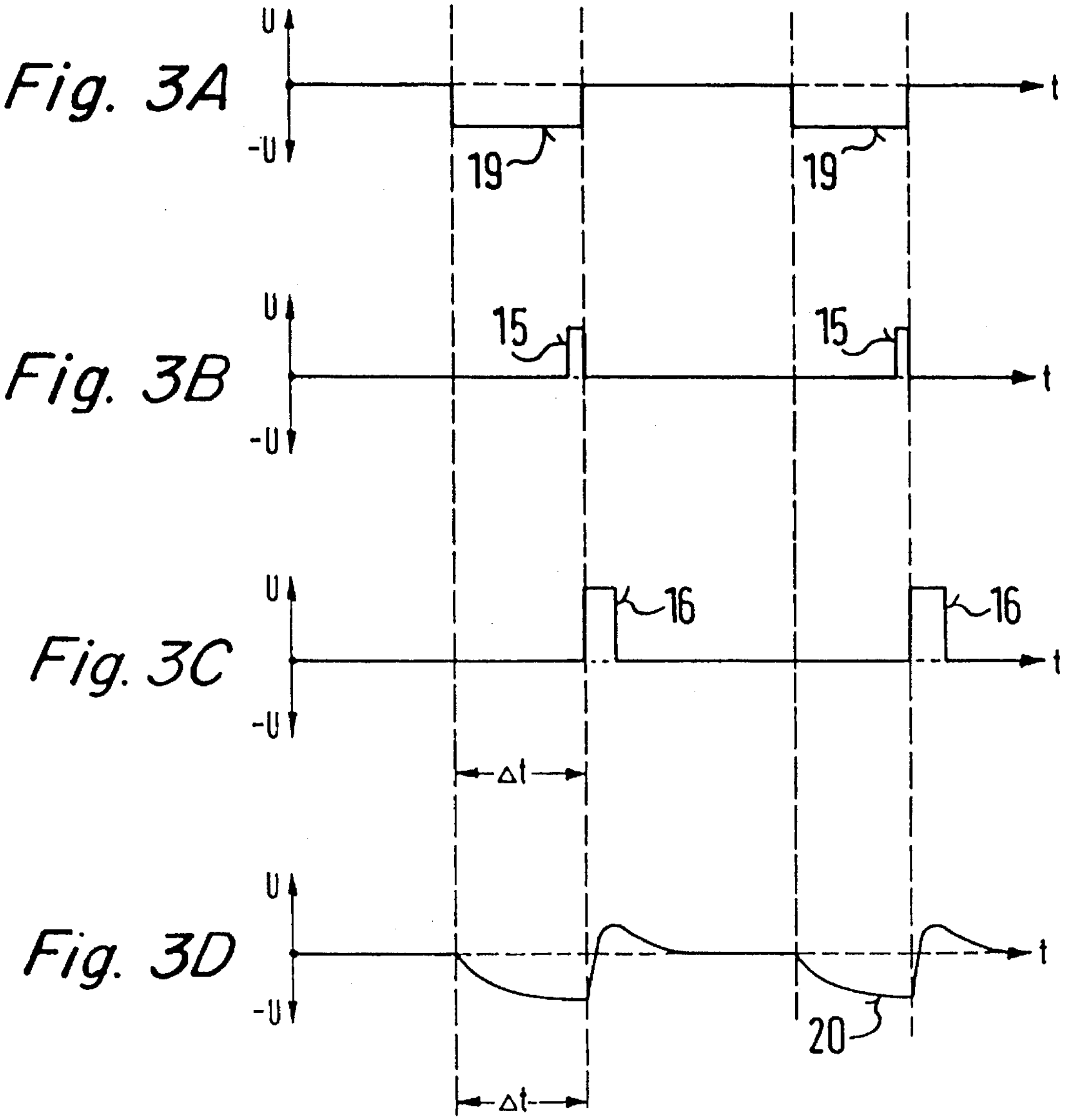
Figures 4A, 4B, 4C, 4D:
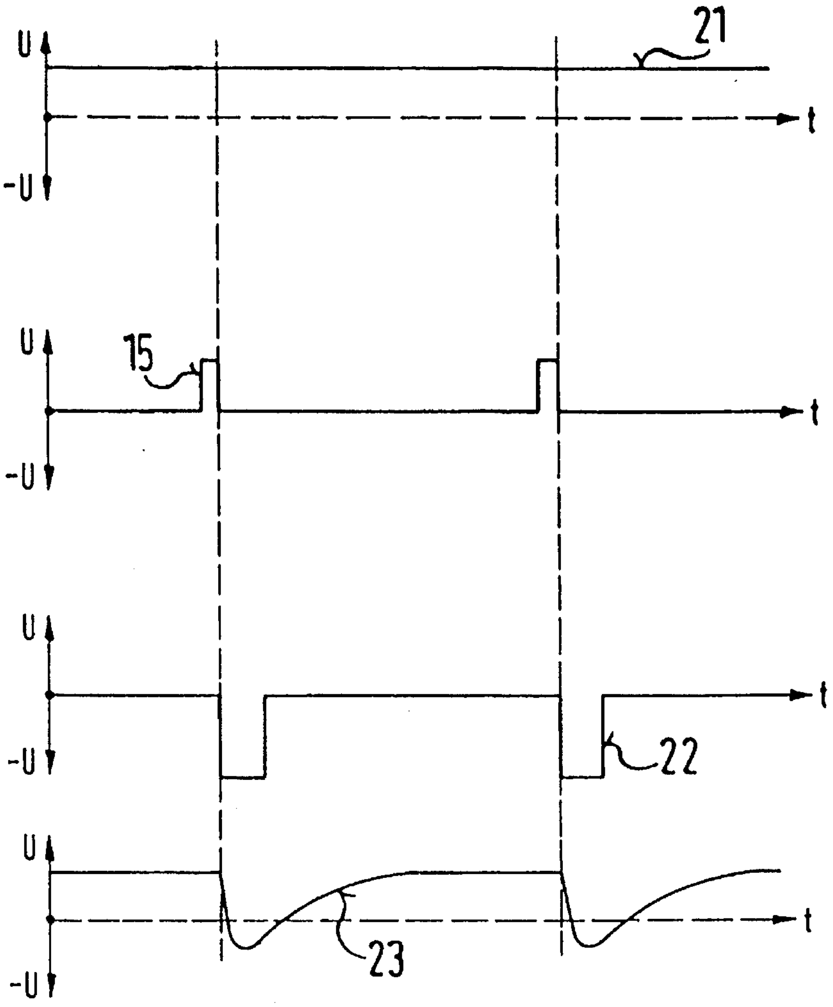
Figures 5A, 5B, 5C, 5D:
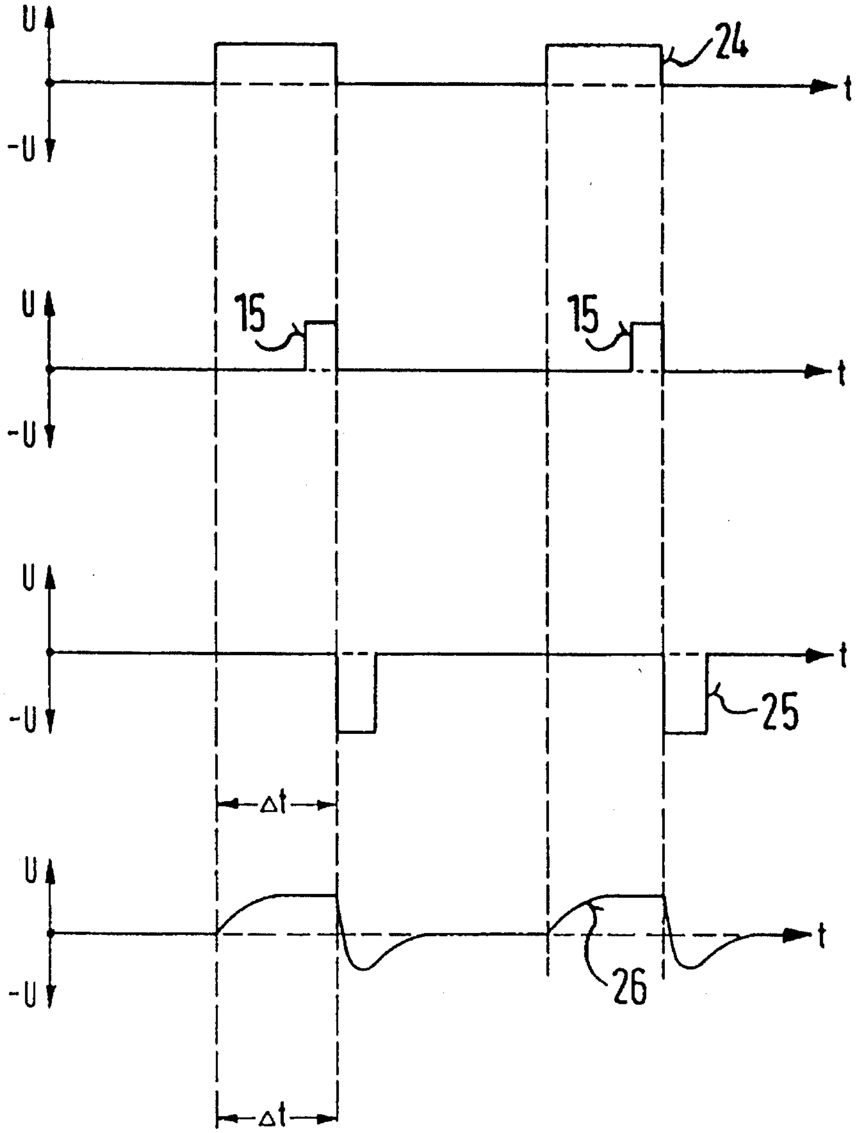

With the circuit shown in FIG. 1, the transducer elements 1 can be negatively biased and then be driven with high-voltage impulses. With the high-voltage source 6, which is negatively connected in relation to the polarization of the transducer elements, the transducer elements are biased via the resistance 7 opposite to their polarization direction, while the capacitor 8 functions as a separating capacitor for the bias potential, which in this case should be a permanent, direct-current voltage.

The charging capacitor 10 is charged via the other high-voltage source 9. A high speed switch 11, formed for example as a spark gap switch, is connected at its trigger input 12 with a conventional trigger circuit (not described further here). By triggering of the switch 11, it is momentarily closed in such a way that the transducer elements are driven in the direction of the polarization via the high voltage existing at the charging capacitor 10 in the form of a positive high-voltage impulse. By means of the resistance 7 and the diode 13, the transducer elements are then returned to the charging condition, which is determined by the permanent bias potential.

Correspondingly, when the transducer elements are positively biased and are to be excited with negative high-voltage impulses, this circuit functions in an equivalent manner such that negatively directed, acoustical impulses or shock waves can be generated. In this case, only the two high-voltage sources 6 and 9 and the diode 8 (polarized in reverse) are to be built into the circuit according to FIG. 1.

For the voltages (U) running over the time t according to FIGS. 2A–D it is assumed that the bias potential 14, provided by the high-voltage source 6, is a negative direct-current voltage. The trigger impulses 15 drive the switch 11 in such a way that, as described earlier, the positive high-voltage impulses 16 are generated, which in this case overmodulate the bias potential 14. This produces the voltage change 17 on the transducer elements which will correspond essentially to the deformation and the change of length 18 of the transducer elements if working in a linear range. Under these assumptions, one can also recognize according to the FIG. 2D that, due to the negative bias potential, a negative offset **18*a* of the transducer elements is produced, and upon appearance of a high-voltage impulse 16 the progression 18*b*** of the change in length of the transducer elements results.

The voltage diagrams according to FIGS. 3A–D result from an impulse-like form of negative bias potential, wherein the bias-potential impulses 19 are terminated at essentially the same time that the high-voltage impulses 16 appear. This requires an additional triggering of the high-voltage source 6 via a switch, and indeed in such a manner that the bias potential or bias potential impulses 19 are generated chronologically and in relation to the high-voltage impulses 16, as shown in FIGS. 3A–D. The voltage trace 20 then arises in the transducer elements, which in this case also will at least essentially correspond to the progression of the change in length of the transducer elements, both in the emission direction and in the opposite direction.

Should the transducer elements 1 be positively biased and then driven with negative high-voltage impulses, the voltage traces represented in FIGS. 4A–D and 5A–D arise According to FIGS. 4A–D, the bias potential 21 is positive. With the trigger impulses 15 the corresponding high-voltage source is temporarily connected to the transducer elements via a switch, in which case negative high-voltage impulses 22 are generated which are superimposed upon the voltage 21. As a result, the voltage 23 will be produced in the transducer elements, so that starting from a positive off-set these elements will be suddenly reduced in their length and will generate negative or tension impulses.

The relationships represented in FIGS. 5A–D arise when the positive bias potential 24 is represented by impulses with which the transducer elements are biased and brought into a positive offset in relation to their neutral starting form. In this case the trigger impulses 15 can connect the bias-potential source at essentially the same time and switch through the high-voltage source for discharging the negative high-voltage impulses 25, so that the voltage 26 rises in the transducer elements.

In measuring the length At of the bias-potential impulses 19 and 24, it should be observed that the high-voltage source for the high-voltage impulses 25 is so triggered that the required bias-potential is applied to the transducer elements before the arrival of each high-voltage impulse. This will be the case when the relationship $\Delta t \geqq 5\tau$ is fulfilled, where $\tau$ is the time constant conditioned upon the parallel switched transducer elements which are behaving like RC-modules.

Figure 6:
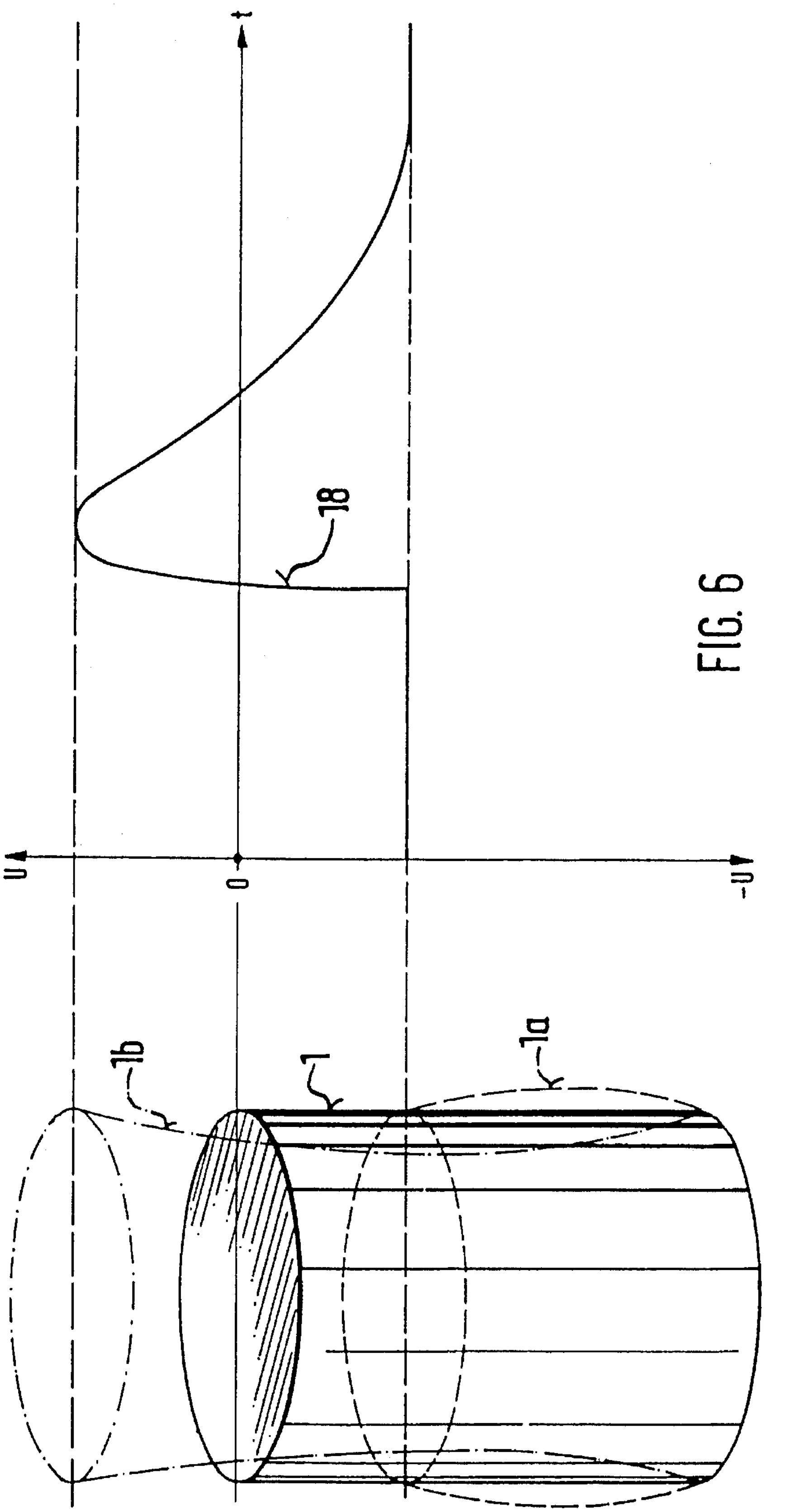
FIG. 6 illustrates a transducer element in relation to a possible path of the voltage effective on it.

From FIG. 6 one can recognize how a transducer element 1 is deformed upon application of a negative bias potential and a positive high-voltage impulse, and how the voltage 18 changes in the transducer element, whereby the voltage will essentially correspond to the time trace of the deformations of the transducer element.

Because of the bias potential (negative and set opposite to the polarization of the transducer element), the transducer element, starting from the contour represented in solid lines in FIG. 6, is shortened in such a way that a negative offset arises with the formation of laterally-directed bulge 1*a*. As soon as the positive high-voltage impulse appears, the transducer element suddenly expands with the formation of a lateral constriction 1*b*, and then assumes again its starting configuration. Understandably, this depends upon whether a permanent or an impulse-type bias potential is applied.

The amplitude of the high-voltage impulses will generally be larger than that of the bias potential and especially when a direct-current voltage is applied as the bias potential to the transducer elements. Moreover, certain limits are to be set on the level of the bias potential by which the depolarizing voltage of the piezo-ceramic is not to be exceeded.

In the represented and described embodiments, all of the transducers elements are simultaneously excited first by the bias potential and afterwards by the high-voltage impulse. It is nevertheless also possible to unite respective pluralities of transducer elements into groups and to drive such groups independently of each other for the emission of sound impulses.

As materials for the transducer elements piezo-electric ceramics are preferred. It is also possible to use electrostrictive materials. Finally, the transducer elements can also be formed as so-called disc packs, that is consisting of a plurality of laminated piezo-ceramic discs.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for generating sound impulses for medical applications, comprising one or more piezo-ceramic transducer elements (1) formed as electro-acoustic transducers, a first high-voltage source (9) with high-voltage impulses (16, 22, 25) for driving the one or more transducer elements, the sound impulses being generated through directed changes in length of the one or more transducer elements dependent on a given polarization of the one or more transducer elements (1) and dependent on the polarity of the high-voltage impulses, and means for charging the one or more transducer elements (1) with a bias potential (14, 19, 21, 24) before the appearance of the high-voltage impulses (16, 22, 25), the polarity of the bias potential being opposite to the polarity of the high-voltage impulse, the charging means providing the bias potential (14, 21) as a permanent direct-current voltage, over which the high-voltage impulses (16, 22) of a greater absolute value are superimposed.

2. A device according to claim 1, further comprising a second high-voltage source (6) for the generation of bias potential (14, 19, 21, 24), and a triggerable switch (12) for connecting the high-voltage source (9) to the one or more transducer elements (1).

3. A device according to claim 1, wherein the sound impulses generated are shock waves for the detection of objects in the interior of a patient body.

4. A device for generating sound impulses for medical applications, comprising one or more piezo-ceramic transducer elements (1) formed as electro-acoustic transducers, a first high-voltage source (9) with high-voltage impulses (16, 22, 25) for driving the one or more transducer elements, the sound impulses being generated through directed changes in length of the one or more transducer elements dependent on a given polarization of the one or more transducer elements (1) and dependent on the polarity of the high-voltage impulses, and means for charging the one or more transducer elements (1) with a bias potential (14, 19, 21, 24) before the appearance of the high-voltage impulses (16, 22, 25), the polarity of the bias potential being opposite to the polarity of the high-voltage impulse, and the charging means providing the bias potential (19, 24) with an impulse form which can be switched off essentially simultaneously with the appearance of the high-voltage impulse (16, 25).

5. A device according to claim 4, wherein the one or more transducer elements (1) function like RC-modules with a time constant $\tau \approx R \times C$, and wherein the length of time $\Delta t$ of the bias potential impulses (19, 24) and the time constant $\tau$ fulfill the relationship $\Delta t \geqq 5\tau$.

6. A device according to claim 4, further comprising a second high-voltage source (6) for the generation of bias potential (14, 19, 21, 24), and a triggerable switch (12) for connecting the high-voltage source (9) to the one or more transducer elements (1).

7. A device according to claim 4, wherein the sound impulses generated are shock waves for the detection of objects in the interior of a patient body.

* * * * *